United States Patent [19]

Hunter et al.

[11] 4,289,652

[45] * Sep. 15, 1981

[54] CATALYST COMPRISING A METAL SUBSTRATE

[75] Inventors: James B. Hunter, Newton Square; George McGuire, West Chester; A. F. D'Alessandro, Havertown; Larry L. Lawlor, Glenmoore, all of Pa.

[73] Assignee: Johnson Matthey Inc., Malvern, Pa.

[*] Notice: The portion of the term of this patent subsequent to Apr. 11, 1997, has been disclaimed.

[21] Appl. No.: 117,555

[22] Filed: Feb. 1, 1980

Related U.S. Application Data

[63] Continuation of Ser. No. 876,565, Feb. 10, 1978, Pat. No. 4,196,099.

[51] Int. Cl.$^3$ ............... B01J 27/14; B01J 22/16; B01J 35/00
[52] U.S. Cl. ............... 252/437; 252/435; 252/467; 252/477 R
[58] Field of Search ............ 252/463, 477 R, 435, 252/437

[56] References Cited

U.S. PATENT DOCUMENTS

| | | | |
|---|---|---|---|
| 3,248,249 | 4/1966 | Collins | 106/286 |
| 3,248,250 | 4/1966 | Collins | 106/286 |
| 3,248,251 | 4/1966 | Allen | 106/286 |
| 3,293,896 | 12/1966 | Kompanek | 72/47 |
| 3,300,331 | 1/1967 | Collins | 117/99 |
| 3,352,814 | 11/1967 | Collins et al. | 260/41 |
| 3,395,027 | 7/1968 | Klotz | 106/1 |
| 3,423,229 | 1/1969 | Kompanek et al. | 117/2 |
| 3,437,605 | 4/1969 | Keith | 252/463 |
| 3,471,413 | 10/1969 | Hervert | 252/477 R |
| 3,656,975 | 4/1972 | Phelps, Jr. | 106/1 |
| 3,719,739 | 3/1973 | Thompson | 423/213.5 |
| 3,867,313 | 2/1975 | Brewer | 423/213.5 X |
| 3,891,575 | 6/1975 | Brautigam et al. | 252/477 R X |
| 3,907,708 | 9/1975 | Lacroix | 423/213.5 X |
| 3,920,583 | 11/1975 | Pugh | 252/465 |
| 3,923,696 | 12/1975 | Chart et al. | 423/213.5 X |
| 3,953,176 | 4/1976 | Santala et al. | 23/288 FC |
| 3,966,645 | 6/1976 | Cairns et al. | 423/213.5 X |
| 3,992,330 | 11/1976 | Noakes et al. | 252/477 R X |

FOREIGN PATENT DOCUMENTS

| | | |
|---|---|---|
| 0825180 | 4/1975 | Belgium. |
| 470894 | 8/1937 | United Kingdom. |
| 690825 | 5/1950 | United Kingdom. |

OTHER PUBLICATIONS

Coating for Industry, Incorporated CFI Bulletin 500 1974.
Technical note D-106 Eubanks et al. Nat. Bureau of Standards NASA Nov. 1959.

Primary Examiner—Delbert E. Gantz
Assistant Examiner—William G. Wright
Attorney, Agent, or Firm—Cushman, Darby & Cushman

[57] ABSTRACT

A catalyst comprising a metal or alloy substrate, an oxidation resistant coating applied to the substrate, the coating comprising aluminum metal powder in a ceramic binder, a high surface area catalytic washcoat over the oxidation resistant coating and a catalytically active material, e.g. a platinum group metal, associated with the washcoat.

5 Claims, 1 Drawing Figure

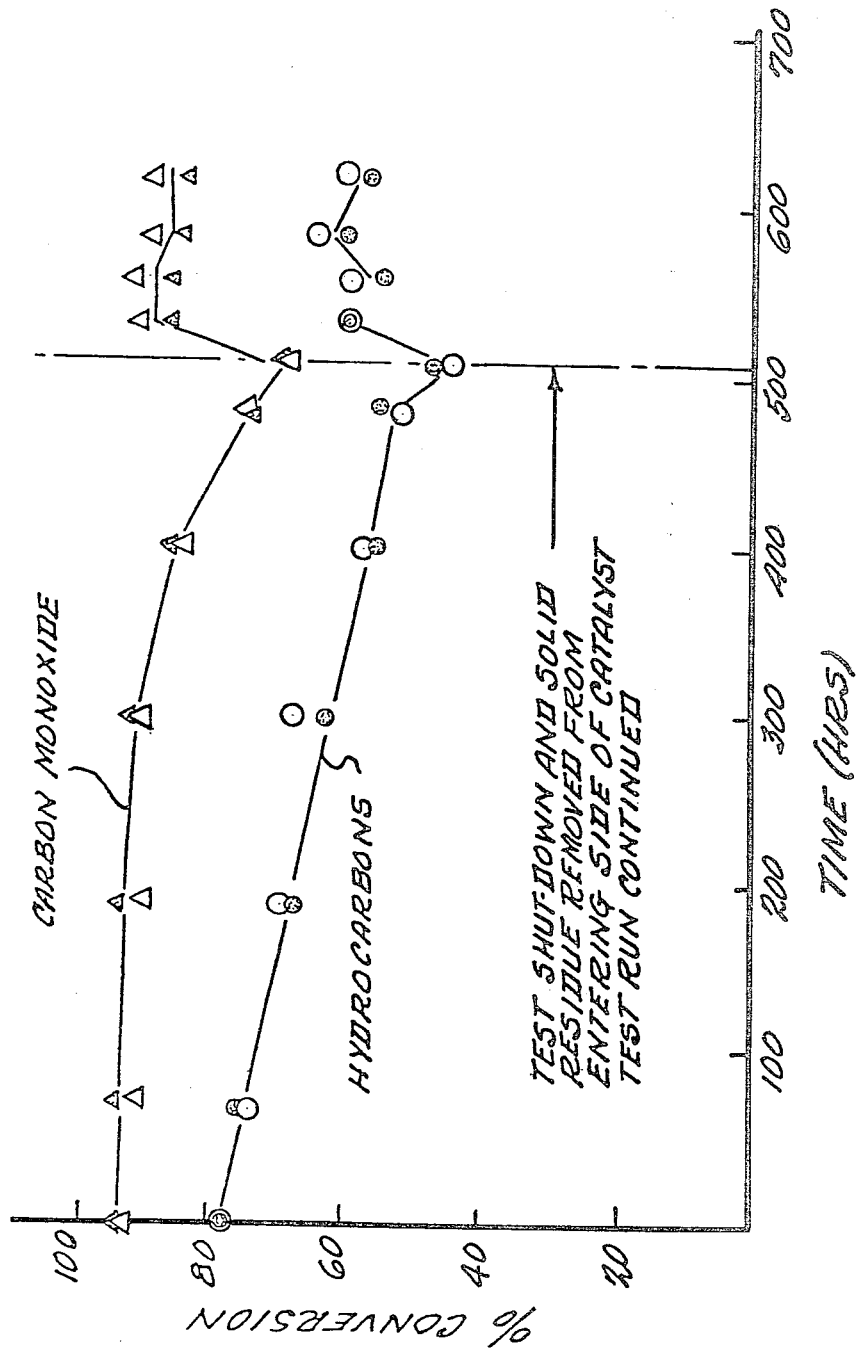

CATALYST COMPRISING A METAL SUBSTRATE

This application is a continuation of U.S. application Ser. No. 876,565, filed Feb. 10, 1978, now U.S. Pat. No. 4,196,099.

FIELD OF THE INVENTION

The invention is concerned with certain advantageous improvements in supported catalysts intended for use at elevated temperatures. More specifically the invention relates to catalysts which are supported on metal substrates. These catalysts are capable of a wide variety of uses at elevated temperatures as will be hereinafter evident. However, a particularly important area of use is in the treatment of automobile exhaust gases or the like to remove air pollutants therein.

It is a well known fact that in recent years, due to environmental restrictions, it has become necessary to catalytically convert various types of noxious exhaust gases into non-toxic or less toxic gases before they are discharged into the atmosphere. For example, it has now become conventional to pass the exhaust gases from an automobile engine or similar type of internal combustion engine through a catalytic converter system before discharge into the atmosphere. These exhaust gases normally contain large amounts of $NO_x$, hydrocarbons and carbon monoxide. However, passage through the catalytic converter reduces the $NO_x$ and/or oxidizes the hydrocarbons and carbon monoxide to carbon dioxide and water.

The catalytic converter used for automobile exhaust gas may comprise a honeycomb structure including substrate which is capable of withstanding the high temperature of the exhaust gas and which has been coated with a catalytically active platinum group metal or metals, e.g. platinum or platinum/rhodium alloy. To increase surface area and to improve adhesion of the catalytic coating to the substrate, a high surface area catalytic "washcoat", usually comprising alumina, is initially applied to the substrate followed by deposition of the platinum group metal (see, for example, U.S. Pat. Nos. 2,580,806; 2,664,340; 2,742,437; 2,742,434; 2,921,035; 3,565,830; 3,920,583 and British Pat. No. 690,825).

The substrate is most usually a ceramic or refractory which can be prepared into a honeycomb or the like having a high surface area. However, there have also been a variety of proposals to use different types of metals or alloys which are oxidation resistant and otherwise capable of withstanding high temperatures as the substrate. In this connection, see, for example, U.S. Pat. No. 3,920,583 which describes a catalyst comprising a substrate made of an alloy or iron, chromium, aluminum and yttrium (commonly called "Fecralloy"), an alumina washcoat and a platinum group metal catalytic surface. According to U.S. Pat. No. 3,920,583, the substrate should be subjected to a heat treatment to develop an aluminum oxide surface which serves to key the washcoat and catalytic surface thereto.

U.S. Pat. No. 3,867,313 also describes a catalyst comprising a heat resistant nickel-free alloy consisting essentially of aluminum, chromium and iron (e.g. "Kanthal" alloys) as the substrate with a noble metal catalytic coating thereon. The catalyst of this patent is an all-metal one and does not apparently include a washcoat. However, the patent does illustrate another prior effort to use a metal alloy as a catalyst substrate.

Other patents which describe various types of catalysts comprising a metal substrate include the following:

U.S. Pat. Nos.
3,231,520
3,437,605
3,712,856
3,719,739
3,773,894
3,891,575
3,907,708
3,923,696
3,953,176
3,957,692
3,966,646
3,992,330
British Pat. No. 470,894

Where the catalyst is to be used at high temperature in the presence of air or oxygen as, for example, in the case of automobile exhaust control, the metal substrate, if used, is normally fabricated from expensive high temperature oxidation resistant metals or alloys (e.g. Fecralloy or Kanthal as mentioned above). It is not, for example, possible to effectively use conventional stainless steel or the like as the substrate for auto exhaust catalysts, at least in the absence of some kind of special treatment, since the stainless steel is incapable of withstanding the high temperatures which are involved. On the other hand, special alloys such as Fecralloy and Kanthal are expensive and the supply thereof is not always adequate. Additionally, in the case of Fecralloy, the heat treatment required to develop the oxide "keying" surface adds to the time and cost involved in preparing the catalyst. There is, therefore, a real need in the art to provide a simple and convenient way of using less expensive metals and alloys which normally do not possess adequate high temperature oxidation resistance, such as stainless steel, as substrates for catalysts to be used at high temperature, e.g. auto exhaust gas catalysts. The principal object of the invention is, therefore, to provide novel catalysts based on stainless steel or the like which are capable of use at elevated temperature. Other objects will also be apparent from the following description of the invention.

SUMMARY OF THE INVENTION

Broadly stated, the invention contemplates rendering a metal which normally would be unsuitable as the substrate for a catalyst to be used at high temperature (e.g. above 1200° F.), suitable for such use by first coating the metal with a thin high temperature oxidation resistant layer, as defined below, prior to conventional washcoating with alumina or other material and application of the catalytically active material, e.g. platinum group metal.

The high temperature oxidation resistant layer is obtained by applying to the metal substrate an aqueous coating composition which is curable at a temperature below 500° F. and may comprise dissolved phosphate, preferably aluminum phosphate; dissolved dichromate or molybdate; solid particulate material such as powdered metal, powdered alloys and refractory metal oxides and a modifier which permits curing into water-insoluble form at a temperature below 500° F. Advantageously the particulate material is aluminum metal powder and the modifier is an amine, preferably an alkanol amine such as diethanolamine.

While a number of coating compositions of the type described above are commercially available and suitable for use herein, a particularly preferred composition is "Alseal-500" which is available from Coatings for Industry, Incorporated, Philadelphia, Pa. The product comprises a dispersion of aluminum metal powder (5 micron size) in an aqueous solution of a chromium salt ($CrO_3$) and a ceramic binder such as aluminum phosphate.

It is understood that Alseal-500 and generally equivalent coating compositions are described in Belgian Pat. No. 825,180, the subject matter of which is incorporated herein by reference. Alseal-500 is described in available trade literature as a high temperature, corrosion and oxidation resistant coating material for ferrous alloys which contains aluminum powder in an organo-inorganic ceramic binder and has the unique characteristic of being curable at temperatures as low as 250° F. when heated at that temperature for 30 minutes. This is low compared to other types of cermet ceramic/inorganic coatings and means that the coatings can be applied and cured at temperatures which would not adversely affect the metal substrate. A further feature of Alseal-500 is that the corrosion and oxidation protection afforded thereby is excellent at high temperatures, e.g. 1200° F.

Details as to the preparation of "Alseal-500" and possible compositional variations therein are not described herein since these are given in Belgian Pat. No. 825,180. However, it is noted that preferred compositions for the organic-inorganic binder, before addition of the aluminum metal particles or equivalent, will generally fall within the following ranges:

|  | Preferred Amounts, GMS |
|---|---|
| dissolved phosphate | about 1 to about 6 |
| dissolved dichromate and/or molybdate | about 0.15 to about 3.5 |
| metal ion | about 1 to about 6 |
| amine | about 0.02 to about 0.3 |

Usually from about 20 to about 2000 g/l of aluminum metal powder or other particulate material will be added to the binder to give the coating composition as used.

The following illustrates one way of preparing an aluminum metal/ceramic coating composition for use herein to give the desired oxidation resistant coating:

An aluminum phosphate/$CrO_3$ solution was prepared by combining 300 g of hydrated alumina ($Al_2O_3.H_2O$) with 558 ml of 75% phosphoric acid and thereafter high speed mixing. After standing overnight the solution was decanted from the insoluble $Al(OH)_3$ which had settled to the bottom. The resulting solution was diluted with water to yield a 60% by weight aluminum phosphate solution. To 100 ml of this solution, 12 g of ($CrO_3$) was added.

An aqueous organic-inorganic binding solution is then prepared by mixing together the following:

| | |
|---|---|
| $H_2O$ | 25 ml |
| aluminum phosphate and $CrO_3$ solution as prepared above | 100 ml |
| $(HOCH_2CH_2)_2NH$ | 3 g |

100 ml of the thus prepared binding solution and 90 g of aluminum metal powder (−400 mesh) are then combined to give a coating composition suitable for use herein.

Other coating compositions containing dissolved phosphate, dissolved dichromate or molybdate, and solid particulate material which may be used herein, preferably with appropriate modification to lower the curing temperature, are disclosed in a publication entitled "Investigation of Aluminum Phosphate Coatings for Thermal Insulation of Air Frames", by Eubanks and Moore, National Aeronautics and Space Administration (NASA Technical Note D-106, 1959) and U.S. Pat. No. 3,248,251 to Allen. Appropriate modifications of these compositions to lower the curing temperature are described in U.S. Pat. Nos. 3,248,250 and 3,248,249. According to U.S. Pat. No. 3,248,250, the curing temperature is lowered by adding an alkali metal silicate while U.S. Pat. No. 3,248,249 proposes the addition of a solid particulate material having a grain size on the order of 0.1 micron or finer to lower the curing temperature.

The metal substrate used herein may be made of any metal (including alloys) which can be fabricated into the desired form (e.g. honeycomb) but which normally would not be sufficiently heat and/or oxidation resistant at high temperature to be suitable for use as a catalyst substrate. Typically suitable are the stainless steels of the 400 series, e.g. stainless steel 420 which is free of nickel and alumunium but has a relatively high chromium content (e.g. 13% Cr, balance essentially iron). Normally stainless steel 420 could not be used as a substrate in the usual way (i.e. by application of washcoat and platinum group metal) as an automobile exhaust gas catalyst because the alloy could not effectively withstand the high temperature of the exhaust gas and exotherms of several hundred degrees during periods of hydrocarbon rich operation. However, application of the oxidation resistant layer, e.g. aluminum/ceramic coating according to the invention, makes it possible to satisfactorily use the alloy as the substrate for an exhaust gas catalyst.

The ceramic coating, e.g. Alseal-500 or the equivalent, may be applied in any convenient fashion, e.g. by spraying to the desired thickness. The coating may be dried by heating at 150°–200° F. for at least 15 minutes (no maximum time) followed by curing at 250°–350° F. for at least 30 minutes, e.g. 4–6 hours (no maximum time). If desired, the coating may be given a further post-firing at about 1025° F. for 60 minutes or more (no maximum time) although this is not necessary. Single or plural coatings may be used. Normally the coating or coatings in the finished catalyst will have a thickness of about 0.5 to about 4 mils, preferably about 1–2 mils. Where multiple coats are applied, curing should be effected after each coating.

The oxidation resistant ceramic coating may be applied to the substrate before or after the substrate is shaped into the desired form. For example, the coating may be applied directly to flat and corrugated strips of metal before rolling to form a honeycomb structure or the honeycomb may be made first followed by application of the oxidation resistant coating.

After application of the oxidation resistant coating, a conventional high surface area refractory oxide washcoat, preferably alumina, is applied in the usual fashion followed by drying and calcining and application of the platinum group metal or metals, all as conventionally employed in the preparation of exhaust gas catalysts (See, for example, U.S. Pat. No. 3,920,583).

The importance of using the aluminum/ceramic coating according to the invention is shown by the fact that after 420 stainless steel is coated with "Alseal-500" and fired at 1100° F., it shows no undesirable effects whatsoever when held overnight at 2000° F. In contrast, 420 stainless steel held overnight at 2000° F. without being coated with "Alseal" is very badly damaged.

The FIGURE discloses a graph of the conversion results of carbon monoxide and hydrocarbons with respect to time.

The invention is illustrated, but not limited, by the following example:

EXAMPLE 1

Two automobile exhaust catalysts A and B were prepared to test their ability to convert hydrocarbons and carbon monoxide in automobile exhaust gas. The catalysts were made by wrapping alternating sheets of flat and corrugated metal around a ¼" mandrel to form cylindrical honeycomb substrates about 3" long and 2" diameter. In one case (catalyst A), representative of the invention, the metal sheets consisted of stainless steel 420 while in the other (catalyst B), the sheets consisted of Fecralloy. The Fecralloy substrate had been heat treated at high temperature to form an aluminum oxide "keying" surface. Catalyst B was completed by dipping the heat treated Fecralloy cylinder in a conventional alumina washcoat, followed by drying, calcining and then depositing platinum group metals (2 parts Pt, 1 part Pd) on the washcoat in conventional fashion.

Catalyst A was prepared by uniformly spraying the stainless steel 420 cylinder with Alseal-500. The thus coated cylinder was dried at 200° F. and cured at 350° F. for 30 minutes. The Alseal-500 coating was about 1-1.5 mil thick after drying and curing. The cylinder was then given a one hour post firing at 1025° F. Washcoat and platinum group metal were then applied exactly as in the case of the Fecralloy substrate.

Catalysts A and B were then connected at one end to the exhaust of a standard 8-cylinder Ford engine. The other end of each catalyst was connected to an analyzer for determining the percent conversion of hydrocarbons (HC) and carbon monoxide (CO) in the exhaust gas. The percent conversions at various times are shown in the following table:

TABLE I

| Hours Operation | 3.5 | 25 | 70 | 140 | 190 | 250 | 300 | 350 | 400 | 440 | 480 | 510 |
|---|---|---|---|---|---|---|---|---|---|---|---|---|
| Catalyst A (stainless steel substrate) % Conversions | | | | | | | | | | | | |
| HC | 79 | 78 | 76 | 71 | 68 | 67 | 64 | 61 | 55 | 57 | 56 | 47 |
| CO | 96 | 95 | 96 | 96 | 95 | 94 | 93 | 88 | 86 | 83 | 76 | 71 |
| Catalyst B (Fecralloy substrate) | | | | | | | | | | | | |
| HC | 79 | 78 | 75 | 70 | 70 | 71 | 69 | 65 | 58 | 58 | 52 | 46 |
| CO | 95 | 92 | 93 | 91 | 92 | 93 | 93 | 90 | 87 | 82 | 75 | 69 |

The catalysts were cleaned and blown out after 510 hours operation to remove particulate or foreign material, e.g. rust and possibly manganese dioxide from gasoline additives, which tended to clog and otherwise reduce the catalyst efficiency. The catalysts were thereafter again connected up and the percent HC and CO determined with the following results:

TABLE II

| Hours Operation | 535 | 560 | 585 | 620 |
|---|---|---|---|---|
| % Conversion | | | | |
| Catalyst A | | | | |
| HC | 61 | 56 | 61 | 58 |
| CO | 88 | 88 | 86 | 85 |
| Catalyst B | | | | |
| HC | 61 | 60 | 65 | 60 |
| CO | 92 | 93 | 90 | 90 |

The results shown in Tables I and II are also illustrated graphically in the attached FIG. 1.

As will be evident from Tables I and II and the drawing, Catalysts A and B are essentially equivalent in terms of HC and CO conversion. Comparison of the test samples also showed them to be in substantially identical condition after the tests. There was no indication of deterioration, corrosion or rusting on either sample. Catalyst A appeared to have a slightly thicker wash coating than the Catalyst B (Fecralloy) unit but this was apparently due to the slightly rougher surface resulting from the Alseal-500 coating. Thus, the use of the Alseal has the advantage of giving an increased washcoat thickness without requiring any change in the washcoat properties. There was also a very tight surface bond between the metal substrate and the washcoat as a result of the Alseal-500 coating. Apparently, the strong bond between the metal substrate and ceramic coating is due to aluminum diffusion and the formation of intermetallic compounds.

EXAMPLE 2

In a further series of tests eight catalysts were made up and tested as automobile exhaust catalysts as in Example 1. The results are shown below in terms of percent hydrocarbon (HC) and carbon monoxide (CO) conversion after the indicated hours of operation:

| Catalyst | Substrate | 50 Hrs. | | 100 Hrs. | | 150 Hrs. | | 200 Hrs. | | 250 Hrs. | | 300 Hrs. | |
|---|---|---|---|---|---|---|---|---|---|---|---|---|---|
| | | HC | CO | HC | CO | HC | CO | HC | CO | HC | CO | HC | CO |
| 1 | Fecralloy | 72 | 94 | 65 | 95 | 61 | 92 | 65 | 90 | 46 | 83 | 53 | 85 |
| 2 | Fecralloy | 68 | 95 | 68 | 94 | 64 | 92 | 65 | 92 | 53 | 85 | 53 | 86 |
| 3 | Fecralloy | 75 | 95 | 70 | 94 | 64 | 92 | 68 | 94 | 49 | 83 | 54 | 83 |
| 4 | Fecralloy | 74 | 96 | 71 | 95 | 67 | 93 | 67 | 93 | 52 | 87 | 54 | 88 |

-continued

| Catalyst | Substrate | 50 Hrs. | | 100 Hrs. | | 150 Hrs. | | 200 Hrs. | | 250 Hrs. | | 300 Hrs. | |
|---|---|---|---|---|---|---|---|---|---|---|---|---|---|
| | | HC | CO | HC | CO | HC | CO | HC | CO | HC | CO | HC | CO |
| 5 | Fecralloy | 69 | 95 | 66 | 92 | 61 | 89 | 61 | 87 | 53 | 83 | 47 | 83 |
| 6 | 420 Stainless Steel No Alseal | 60 | 80 | 63 | 82 | 63 | 85 | 64 | 84 | 66 | 85.5 | 54 | 85 |
| 7 | 420 Stainless Steel with Alseal | 62 | 92 | 60 | 86 | 59 | 88 | 64 | 88 | 68 | 85 | 63 | 86 |
| 8 | 420 Stainless Steel with Alseal | 73 | 94 | 69 | 93 | 68 | 92 | 66 | 92 | 70 | 90 | 62 | 91 |

The "Fecralloy" substrate used in catalysts 1-4 was prepared by subjecting the alloy to oxidation at 1200° C. for 1 hour to develop a protective oxide coating thereon. In the case of Catalyst 5, the Fecralloy substrate was coated with a Ce-Sol. In catalysts 6-8, the stainless steel was heated to 850° F. and after application of the "Alseal" in the case of Nos. 7 and 8, the substrate was further heated at 1000° F.

The tabulated results show that the "Alseal" catalysts according to the invention retained their effectiveness over the 300 hour test period.

Various modifications may be made in the invention as described in the foregoing. Thus, while the catalyst has been described in connection with the treatment of automobile exhaust gas for the control of hydrocarbon and carbon monoxide pollutants, the catalyst may be used for other purposes. For example, the present catalyst may be used in processes involving catalytic (flameless) combustion, ammonia oxidation, high temperature catalytic oxidations other than automobile exhaust control (e.g. fume and/or odor abatement), high temperature catalytic hydrogenation including methanation, Fischer Tropsch reaction, coal liquefaction, nitric oxide abatement, and the like. More specifically, methanation and Fischer Tropsch reactions can be carried out by contacting CO and $H_2$ gas, with or without added steam, with the present catalyst. Nitric acid may be prepared by contacting ammonia and oxygen, e.g. air, with the catalyst under otherwise conventional conditions. Catalytic combustion may be carried out by contacting the appropriate fuel/air (or oxygen) mixture with the catalyst. Additionally, it is noted that, while the invention is of particular importance for use with stainless steel and/or other metals or alloys which are not normally oxidation resistant at high temperatures, the invention may also be used in applications involving alloys which have high temperature oxidation resistance, e.g. the Kanthal or Fecralloy type alloy, where, for example, a particularly high level of bonding may be desired between the catalytic material and the substrate.

Accordingly, the scope of the invention is defined in the following claims wherein:

We claim:

1. A supported catalyst suitable for use at a temperature above 1200° F. consisting essentially of a metal or alloy substrate which itself is not heat or oxidation resistant at a temperature above 1200° F.; a heat-cured oxidation resistant coating applied to said substrate, said coating being applied as an aqueous coating composition which is curable into water-insoluble oxidation resistant form by heating and which consists essentially of a dispersion of aluminum metal powder in an aqueous chromium-containing/aluminum phosphate binder composition; a high surface area refractory oxide washcoat over said oxidation resistant coating and a catalytically active platinum group metal deposited on said washcoat.

2. A catalyst according to claim 1 wherein the substrate is a stainless steel.

3. A catalyst according to claim 2 wherein the substrate is stainless steel 420.

4. A catalyst according to claim 1 wherein the catalytically active material comprises one or more platinum group metals or combination of PGM's with other catalytic materials.

5. In a supported catalyst which is suitable for use at elevated temperatures comprising a metal or alloy substrate which itself is not heat or oxidation resistant at the temperature of use and which is used to support a catalytically active platinum group metal supported on said substrate, the improvement which comprises a heat-cured oxidation resistant coating applied to said substrate between the substrate and the platinum group metal to protect the substrate, said coating being applied as an aqueous coating composition which is curable into water-insoluble oxidation resistant form by heating and which consists essentially of a dispersion of aluminum metal powder in an aqueous chromium-containing/aluminum phosphate binder.

* * * * *